(12) United States Patent
Ohanyan (10) Patent No.: US 11,529,136 B2
(45) Date of Patent: Dec. 20, 2022

(54) SUTURE HOOK TOOL

(71) Applicant: Vahagn Ohanyan, Hudson, OH (US)

(72) Inventor: Vahagn Ohanyan, Hudson, OH (US)

(*) Notice: Subject to any disclaimer, the term of this patent is extended or adjusted under 35 U.S.C. 154(b) by 77 days.

(21) Appl. No.: 16/829,897

(22) Filed: Mar. 25, 2020

(65) Prior Publication Data

US 2020/0315609 A1 Oct. 8, 2020

Related U.S. Application Data

(60) Provisional application No. 62/823,260, filed on Mar. 25, 2019.

(51) Int. Cl.
*A61B 17/04* (2006.01)

(52) U.S. Cl.
CPC ...... *A61B 17/0482* (2013.01); *A61B 17/0483* (2013.01)

(58) Field of Classification Search
CPC ............ A61B 17/0483; A61B 17/0482; A61B 17/0469; A61B 17/06061; A61B 17/062; A61B 17/3468; A61M 37/0069; A61F 2/0004
See application file for complete search history.

(56) References Cited

U.S. PATENT DOCUMENTS

| | | | | |
|---|---|---|---|---|
| 5,350,385 A * | 9/1994 | Christy | ............ | A61B 17/06109 606/139 |
| 5,741,276 A * | 4/1998 | Poloyko | ............... | A61B 17/062 606/139 |
| 8,123,762 B2 * | 2/2012 | Chu | .................... | A61B 17/0469 606/144 |
| 9,220,496 B2 * | 12/2015 | Martin | ............. | A61B 17/06114 |
| 9,381,075 B2 * | 7/2016 | Chu | .................... | A61B 17/0482 |
| 2006/0111732 A1 * | 5/2006 | Gibbens | ............. | A61B 17/0482 606/145 |
| 2012/0158009 A1 * | 6/2012 | Ostrovsky | ......... | A61M 37/0069 606/108 |
| 2012/0197281 A1 * | 8/2012 | Chu | ....................... | A61F 2/0004 606/185 |
| 2014/0222033 A1 * | 8/2014 | Foerster | ............. | A61B 17/0469 606/144 |
| 2019/0200976 A1 * | 7/2019 | Kumar | ............. | A61B 17/06109 |

\* cited by examiner

*Primary Examiner* — George J Ulsh (57) ABSTRACT

A suture tool includes a handle portion and a hook portion. The handle portion is preferably a solid shaft of metal material enabling handling by the surgeon. An outside surface of the hook portion is interconnected to one end of the handle portion. The hook portion comprises a hollow U-shaped tube of medical grade stainless steel.

14 Claims, 7 Drawing Sheets

SUTURE HOOK TOOL

CROSS REFERENCE TO RELATED APPLICATION

This application claims priority from U.S. Provisional Patent Application Ser. No. 62/823,260 filed Mar. 25, 2019, and the entirety of which is incorporated herein by reference.

FIELD

The present application relates generally to a surgical tool, and more particularly, to a vascular hook for use in placing sutures around a small vessel during a surgical procedure.

BACKGROUND

In order to conduct a variety of preclinical research, it is necessary to perform small animal surgical procedures. In certain procedures, it is necessary to tie off portions of the animal's vasculature in order to perform the necessary experiments and surgical procedures. Because of the small size and delicate nature of the vascular system of small rodents, damage such as puncturing can result to veins or arteries when suture material is attempted to be inserted or poked into the desired location within the animal.

Given the disadvantages of potentially puncturing delicate vessels of such small animals, a safer, easier and faster system for tying off such vessels during surgery is needed.

SUMMARY OF THE INVENTION

A new surgical tool is provided for use in research laboratories which require animal veins or arteries to be tied off during surgery, such as in cardiovascular and pulmonary research labs. The surgical tool is a vascular hook useful for placing small sutures around small vessels during surgical procedures. Using this surgical tool provides a safer method for tying off blood vessels, while also reducing the amounts of expensive suture used during such procedures.

The suture tool includes a handle portion and a hook portion. The handle portion is preferably a solid shaft enabling handling by the surgeon. An outside surface of the hook portion is interconnected to one end of the handle portion. The hook portion comprises an open ended, hollow tube with an internal passage having a U-shaped, C-shaped or semicircular shaped configuration. Suture material may be threaded through or pass through the internal passage of the hook portion during a surgical procedure. The hook portion may be secured to the handle portion at any location and at any desirable angle, but is preferably secured with one end of the handle portion near the end of one leg of the U-shaped configuration, and with the hook portion at an angle of less than 45 degrees out of the horizontal plane of the handle portion.

DETAILED DESCRIPTION

The new surgical suture hook tool 10 of this application is shown in FIGS. 1-5. Reference numerals with a prime designation are used throughout to indicate alternate but similar structural features or embodiments of the tool 10. The tool 10 is preferably manufactured of medical grade stainless steel, but could be manufactured of any suitable material for a surgical tool that may be economically sterilized for reuse. The tool 10 includes a handle portion 12 and a hook portion 20. The handle portion 12 has a central axis 13 and is preferably a solid shaft of metal material enabling handling by the surgeon, and potentially including a surface texture for ease of handling. An outside surface 21 of the hook portion 20 is interconnected to one end 14 of the handle portion 12, whether by a weld or weld joint 18, or other appropriate permanent connection.

Figure 1:
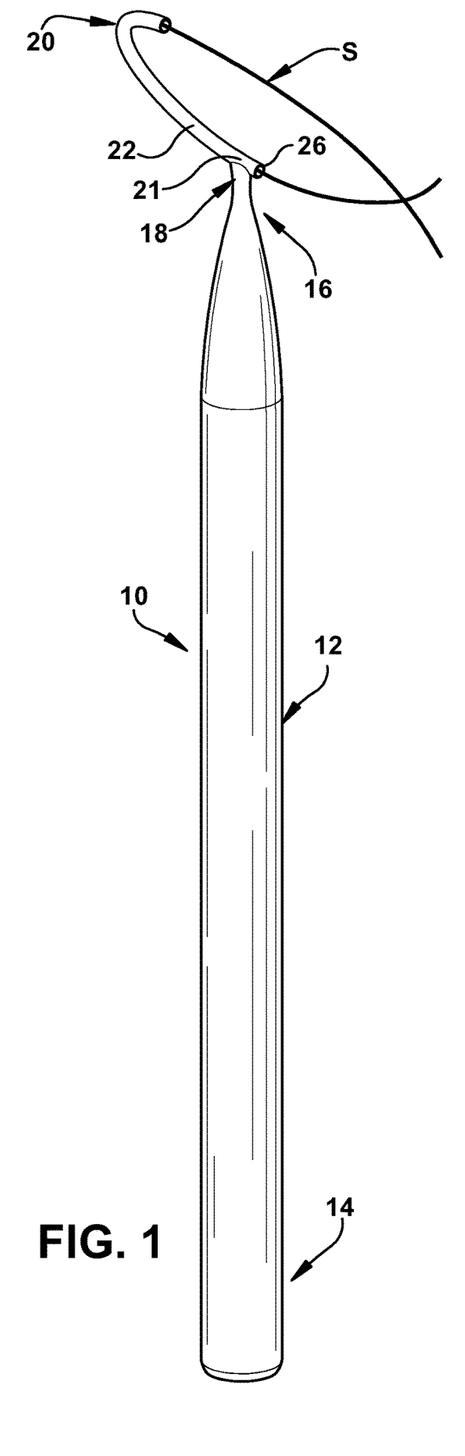
FIG. 1 shows a perspective side view of the new suture tool of this application, showing the internal diameter openings of the hook portion, with a length of suture material extending through the internal passage of the hollow, U-shaped hook portion, and from each end of the hook portion.
Figure 2:
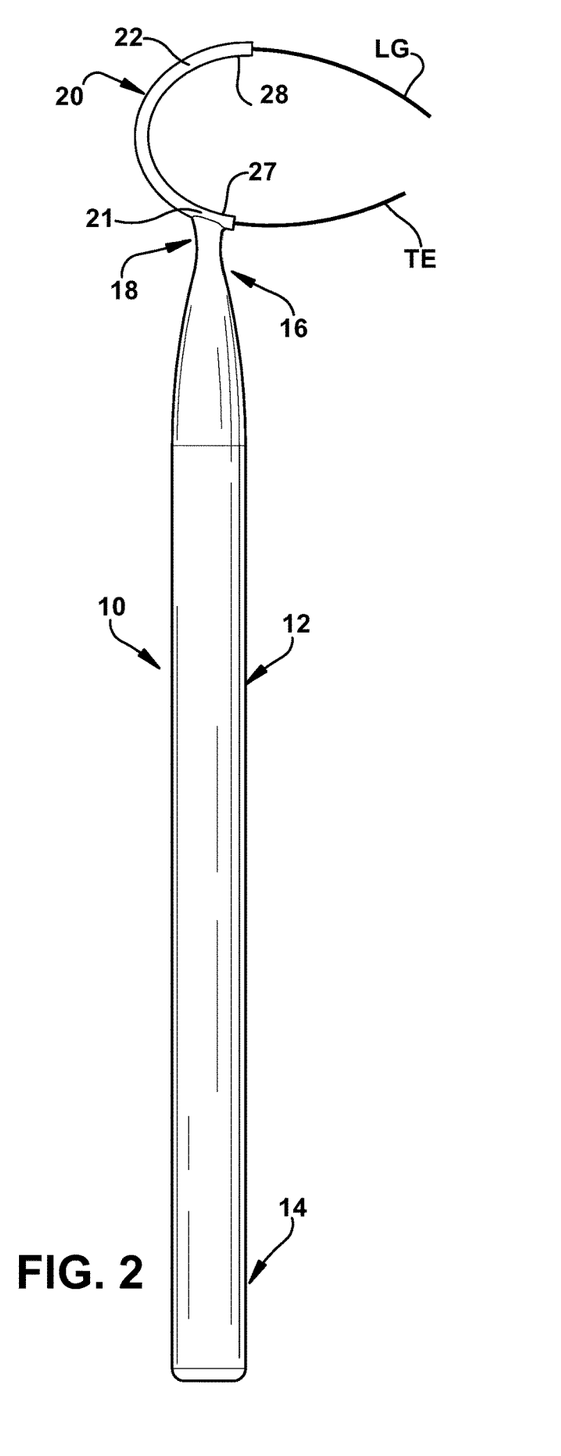
FIG. 2 shows a back view of the tool of FIG. 1.
Figure 3:
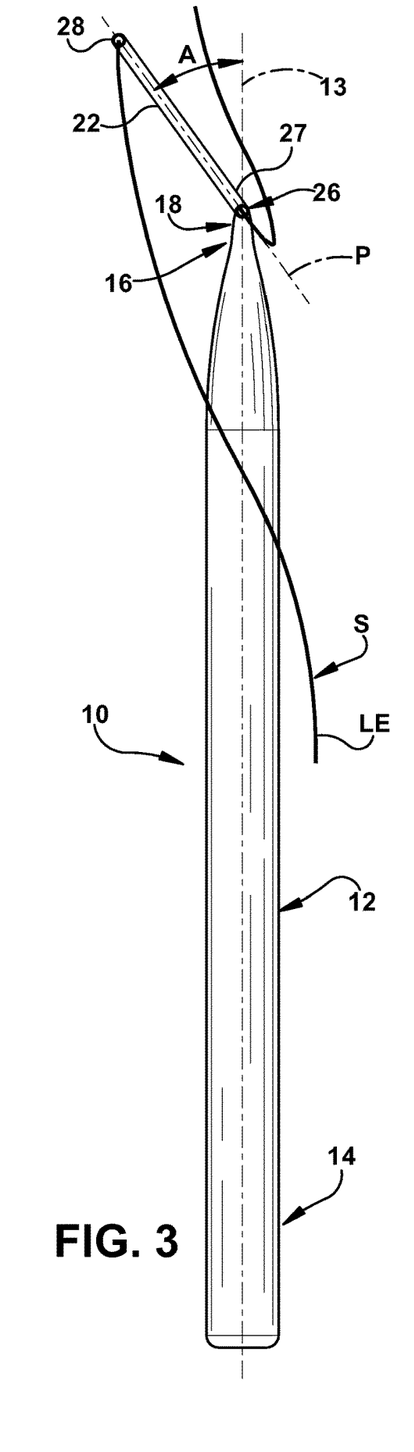
FIG. 3 shows a right side view of the tool if FIG. 1.
Figure 4:
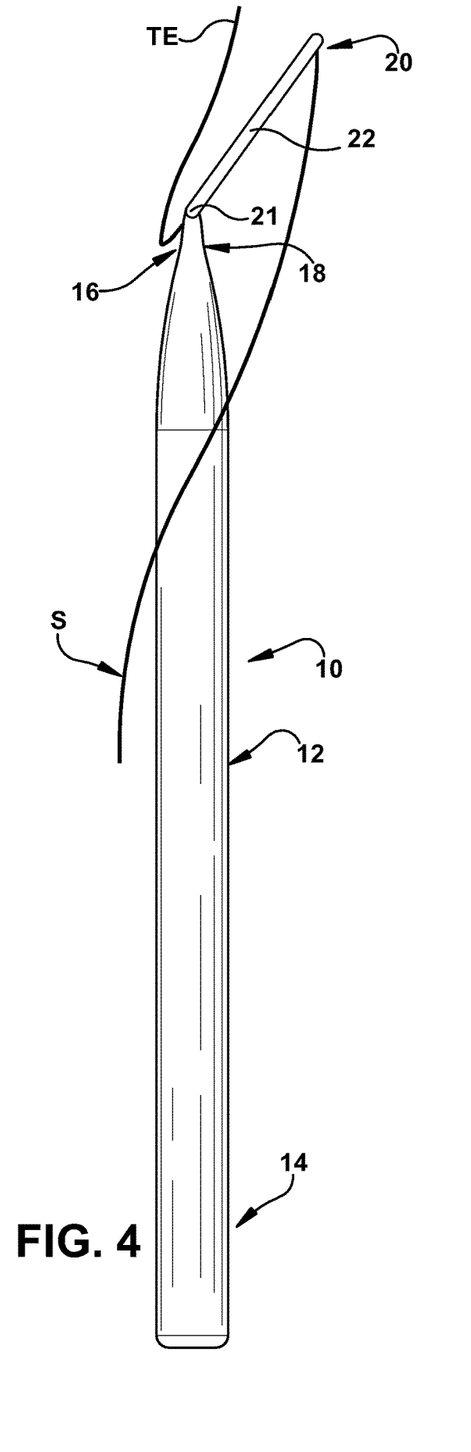
FIG. 4 shows a left side view of the tool of FIG. 1.
Figure 5:
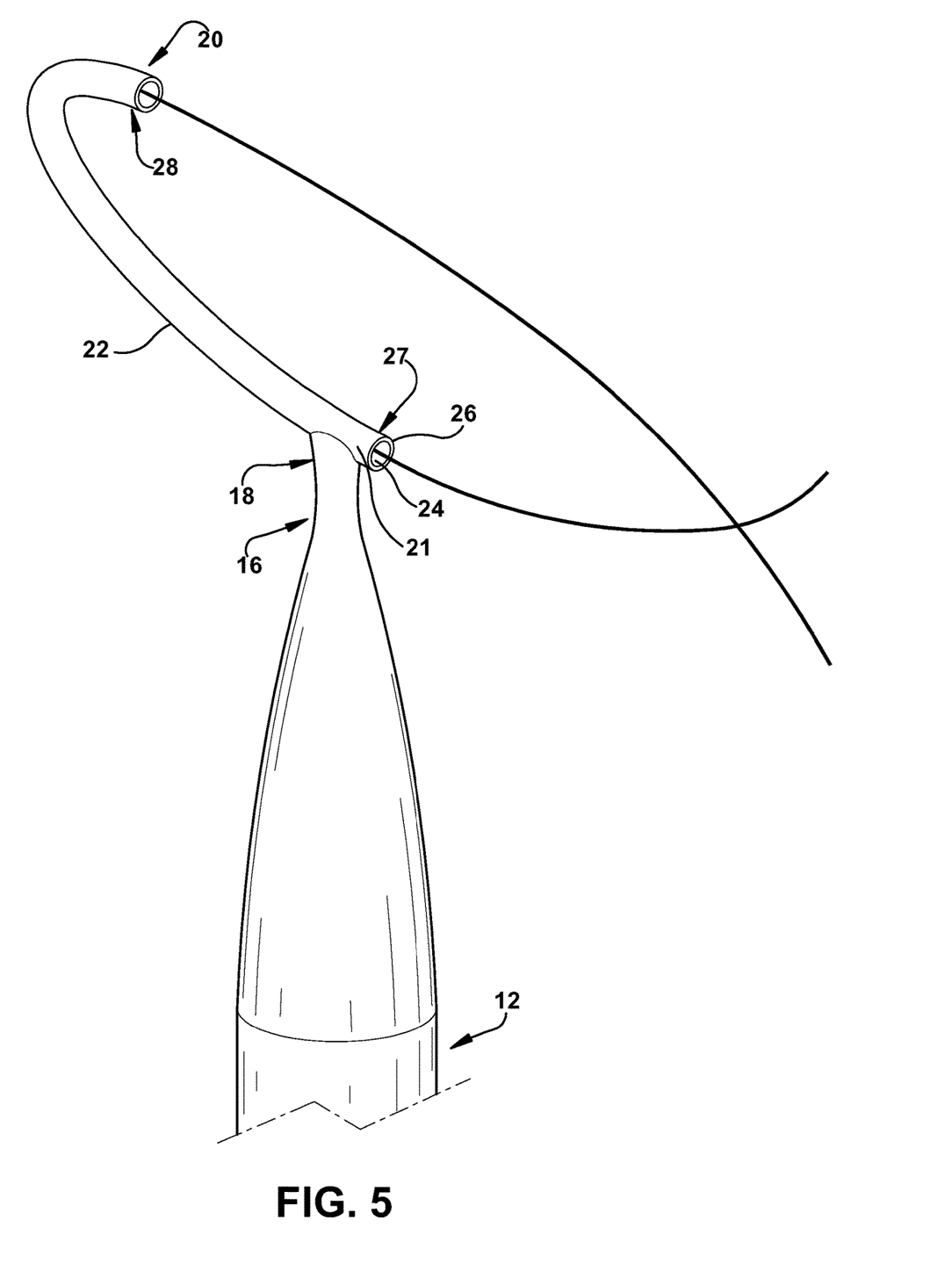
FIG. 5 shows a partial enlarged view of the hook portion of the tool of FIG. 1.
Figure 6:
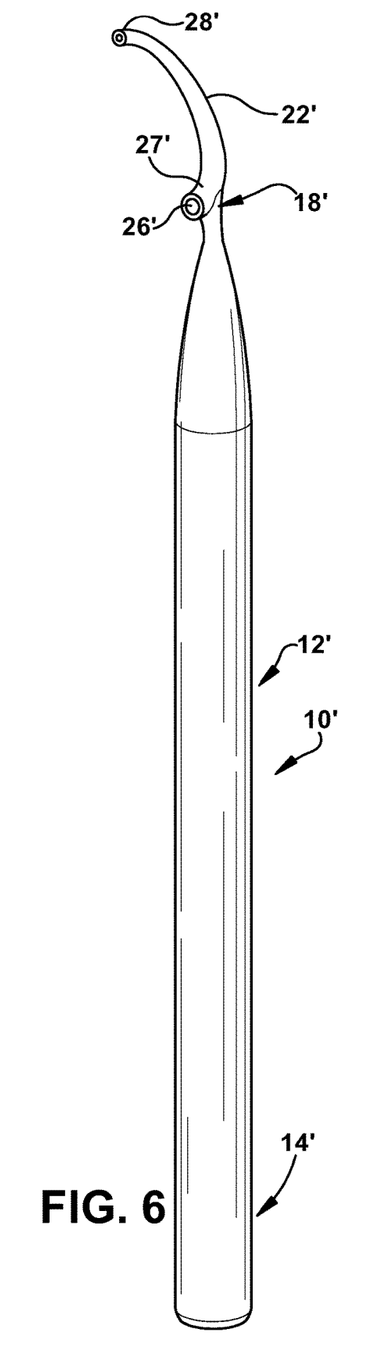
FIGS. 6-8 show an alternate embodiment of the new suture tool in a perspective side view, right side view and back view, respectively, having variable internal and external diameters of the hook portion.
Figure 7:
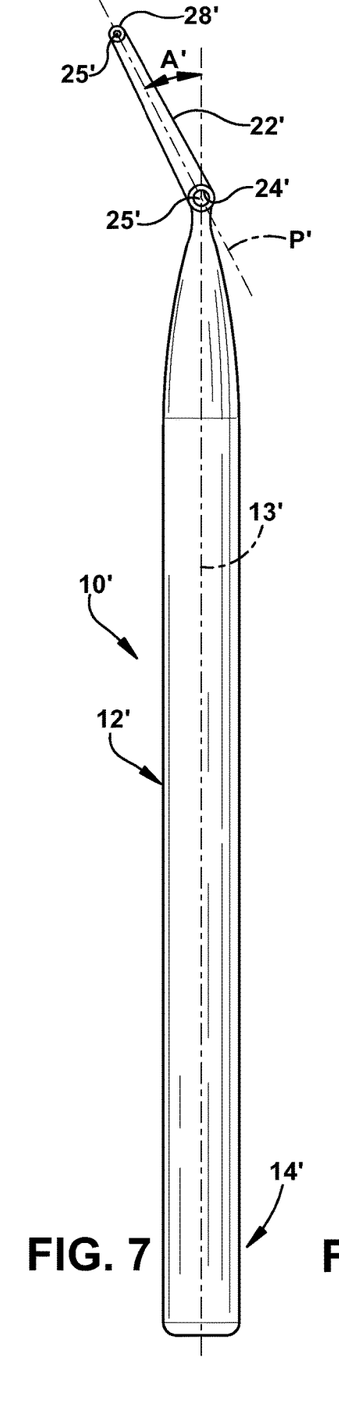
Figure 8:
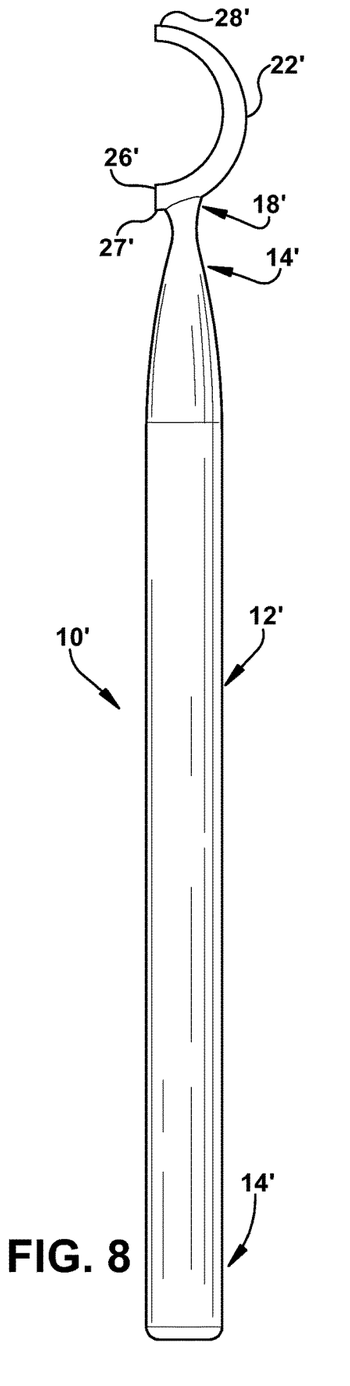
Figure 9:
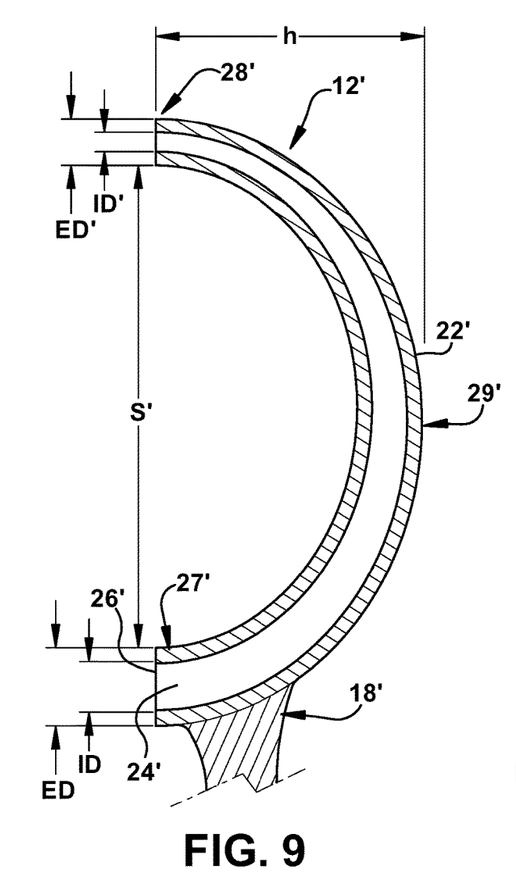
FIG. 9 illustrates a close-up, partial, cut-away taken along the line 9-9 of FIG. 7.

The hook portion 20 comprises an open ended, hollow tube 22 of medical grade stainless steel having a U-shaped, C-shaped or semicircular configuration with one leg 27 and a second free leg 28. An internal passage 24 within the hollow tube 22 has a central axis 25 provided within a plane P. The hook portion 20 may be secured to the handle portion 12 at any location and at any desirable angle, but is preferably secured with one end 14 of the handle portion near an open end 26 of one leg 27 of the U-shaped tube 22. The angle of attachment of the hook portion 20 to the handle portion 12 is such that the central axis 13 of the handle portion is preferably at an angle A of approximately 45 degrees or less with respect to the plane P of the central axis 25 of the internal passage 24 of the hook portion 20, as shown in FIGS. 3 and 7.

Figure 10:
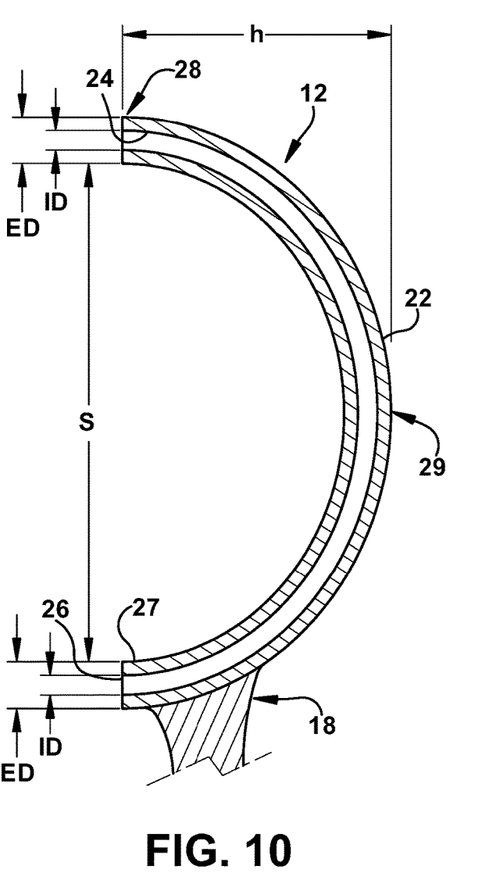
FIG. 10 illustrates a close-up, partial, cut-away view taken along the line 10-10 of FIG. 3.
Figure 14:
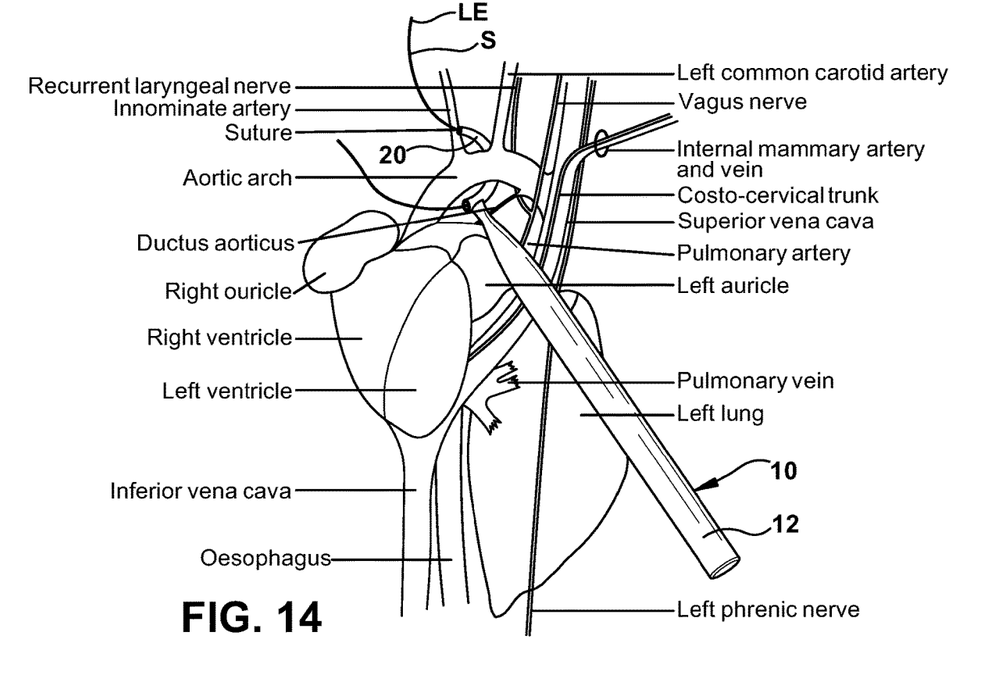

As shown in FIG. 10, the dimensions of the U-shaped tube 22 of the hook portion 20 are preferably provided with an internal diameter ID of approximately 0.2 mm, but the internal diameter may also range from between approximately 0.1 mm to 0.6 mm. As shown, an external diameter ED is preferably provided of approximately 0.4 mm, but may range from approximately 0.2 mm to 1.0 mm. It should be understood that the internal diameter ID of the internal passage 24 of the hook portion 20 may be of any internal diameter sufficient to accommodate suture material S readily passing through the tube 22. Additionally, a spacing S of approximately 4-7 mm may be provided between the legs 27, 28 of the U-shaped tube 22, and a height h from a base or valley 29 of the U-shaped tube 22 to the top of the legs 27, 28 of approximately 2-3 mm. While the preferred embodiment of the tube 22 is illustrated as a semicircle, it should be understood that a crescent, or other similar shape having legs of different lengths or sizes may also be provided, for example, as shown in FIG. 14.

Alternatively, in another tool embodiment shown in FIGS. 6, 7, 8 and 9, the hook portion 20' of the tool 10' may be provided with an internal passage 24' having a smooth tapered structure. In this embodiment, the external and internal diameters, ED', ID' of one leg 27' of the U-shaped hook portion 20' attached to the handle portion 12' is approximately 0.4 mm and 0.25 mm, respectively. In this tapered embodiment of the hook portion 20', the external and internal diameters, ED", ID" of the free leg 28' of the U-shaped hook portion 20' are approximately 1 mm and 0.6 mm, respectively. A gradual internal tapered shape or internal passage 24' is provided between the attached one leg 27' and the free leg 28' of the hook portion 20'. With a tapered internal diameter hook portion 20', the suture material S may be more easily threaded into the larger internal diameter opening ID' in the one leg 27' of the hook portion 20'.

During a surgical procedure, a length of suture material S is cut with a leading end LE and a trailing end TE. The leading end LE of the length of suture material S is inserted into the opening 26 of the one leg 27 of the U-shaped tube 22 attached to the handle portion 12. The leading end LE of the suture material S preferably remains within the tube 22 until the free leg 28 of the tube 22 is placed surrounding the desired animal vessel, while the trailing end TE of the suture material S continues to extend from the open end 26 of the one leg 27, and can be grasped by the surgeon.

Figure 12:
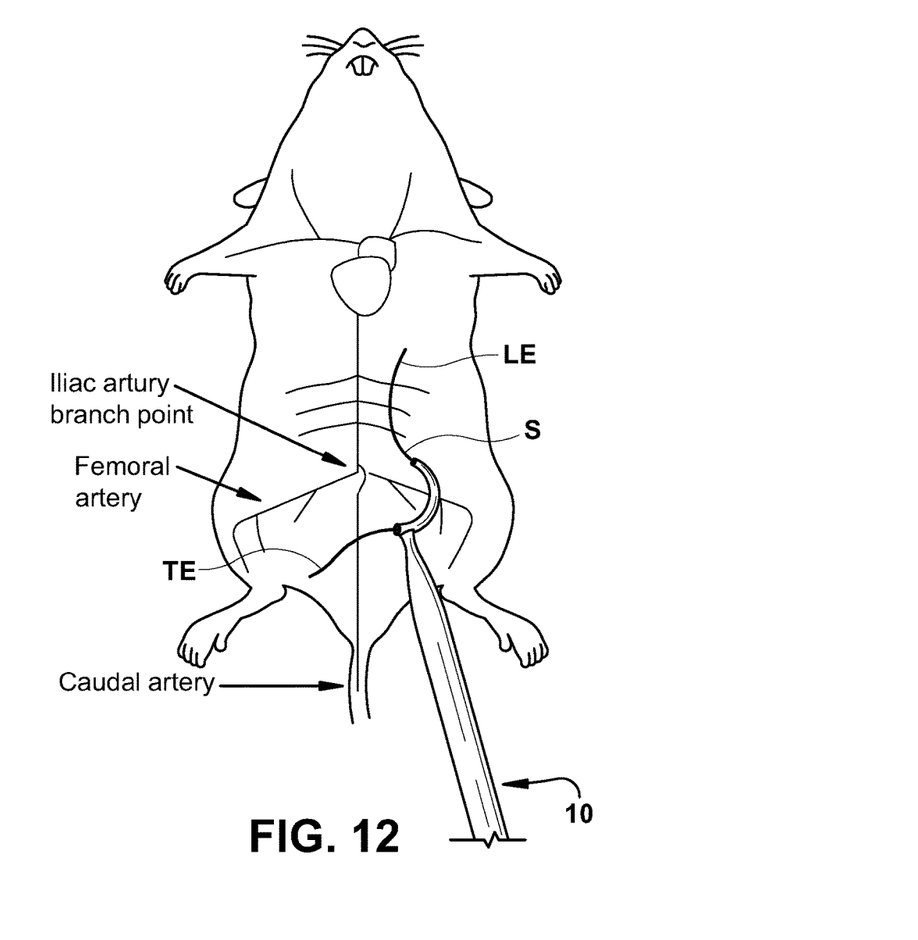
FIG. 12 schematically illustrates use of the suture hook tool shown engaged surrounding a femoral artery of a research animal prior to removal of the tool and tying off of the suture material.
Figure 13:
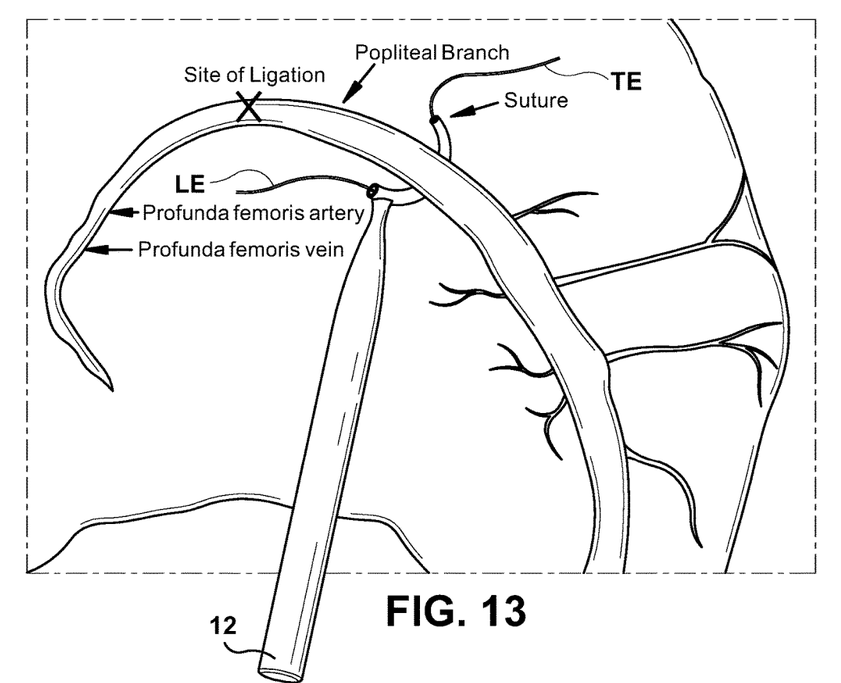
FIGS. 13-14, similar to FIG. 12, schematically illustrate alternate placement of the suture hook tool surrounding vessels to be tied off during a surgical procedure.

Once the suture material S is within the hollow U-shaped tube 22 of the hook portion 20, the free leg 22 of the U-shaped tube 22 is then moved under and around the desired animal vessel until the end of the free leg 28 is visible, called the suture position. In this suture position, the legs 27, 28 of the U-shaped tube 22 are positioned surrounding, or on opposite sides of, the desired animal vessel that is to be tied off with the suture material S. Once in the suture position, the leading end LE of the suture material S may be pushed through and out of the free leg 28 of the tube 22, as shown in FIGS. 12-14. The leading end LE of the suture material S may then be grasped by the surgeon.

Once the surgeon grasps the leading end LE of suture material S extending from the free leg 28, the tool handle portion 12 is used to remove the hook portion 20 from the suture position, while the trailing end TE of the suture material S is removed from the U-shaped tube 22 of the hook portion 20, and may also be grasped. The surgeon may then remove or discard the suture tool 10. Now grasping and pulling both ends LE, TE of the suture material S, the desired animal vessel is tied off by a surgical knot formed with the leading and trailing ends of the suture material, to maintain the suture material in the desired position with the vessel. The process of using the suture hook tool may then be repeated at additional ligation sites, as desired, and as indicated in FIG. 13, to obtain the desired surgical purpose.

Figure 11:
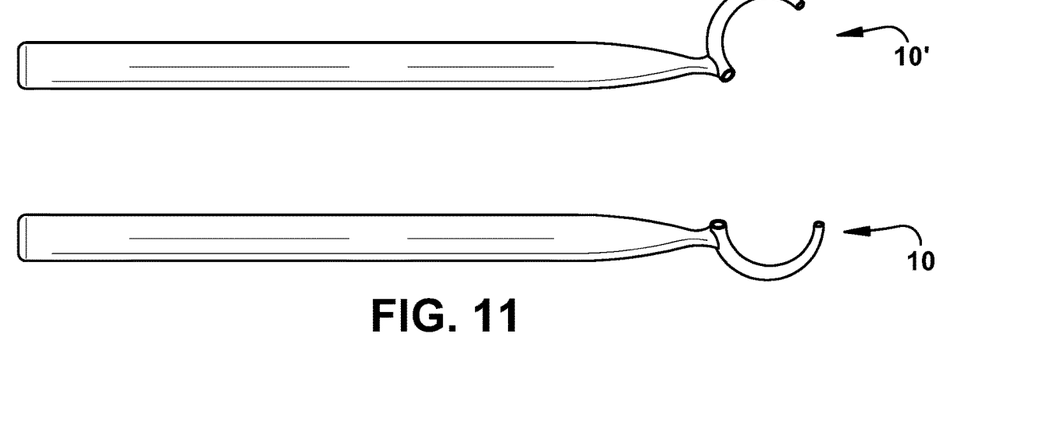
FIG. 11 illustrates top views of the suture hook tool embodiments comparing a hook portion attached for use as a left hand tool and a hook portion attached for use as a right hand tool.

It should be understood, as shown in FIG. 11, that the suture tools 10, 10' may be manufactured with the hook portion 14 extending from the handle portion 12 in a right hand direction or loop, and in a left hand direction or loop, for use on opposing vessels or by right or left handed surgeons. By using the new vascular suture tool 10, 10' shown and described, researchers or surgeons will be able to quickly and easily tie off vessels without injury to the animal, and the suture tool may be readily sterilized for reuse.

While certain embodiments of the invention have been described with specificity in order to improve understanding of the invention, many variations and modifications will become apparent to a person of ordinary skill in the art. It is therefore expected and intended that the certain changes and modifications may be practiced which will still fall within the scope of the appended claims.

I claim:

1. A suture tool comprising: a handle portion having a first end and a hook end; an open ended, hollow, U-shaped tube hook portion having an open attached end connected to the hook end of the handle portion, a an open free end, and having an internal passage within the open ended, hollow, U-shaped tube hook portion extending between the open attached end and the open free end for passing a length of suture material into the internal passage through the open attached end to exit through the open free end; and wherein the handle portion has a central axis, and the internal passage of the open ended, hollow, U-shaped tube hook portion has a central axis provided within a plane positioned at an angle of approximately 45 degrees or less with respect to the central axis of the handle portion; and wherein the open attached end extends past the central axis of the handle portion.

2. The suture tool of claim 1, wherein the internal passage of the open ended, hollow, U-shaped tube hook portion has a constant internal diameter extending from the open attached end to the open free end.

3. The suture tool of claim 2, wherein the internal passage of the open ended, hollow, U-shaped tube hook portion has a constant internal diameter of approximately 0.1 mm to 0.6 mm.

4. The suture tool of claim 3, wherein the spacing between the open free end and the open attached end of the open ended, hollow, U-shaped tube hook portion is approximately 4.0 mm and 7.0 mm.

5. The suture tool of claim 4, wherein the spacing between a base of the open ended, hollow, U-shaped tube hook portion and the open free and open attached ends of the open ended, hollow, U-shaped tube hook portion is approximately 2.0 mm to 3.0 mm.

6. The suture tool of claim 1, wherein the internal passage of the open ended, hollow, U-shaped tube hook portion is tapered from a larger internal diameter at the open attached end to a smaller internal diameter at the open free end.

7. The suture tool of claim 6, wherein the larger internal diameter of the internal passage of the open ended, hollow, U-shaped tube hook portion is approximately 15 mm and the smaller internal diameter of the internal passage of the open ended, hollow, U-shaped tube hook portion is approximately 11 mm.

8. A suture tool comprising: a handle portion having a central axis, a first end and a hook end; an open ended, hollow, U-shaped tube hook portion having an open attached end connected to the hook end of the handle portion, a an open free end, and an internal passage between the open attached end and the open free end for passing a length of suture material into the internal passage from the open attached end to the open free end; and wherein the internal passage of the open ended, hollow, U-shaped tube hook portion has a central axis provided within a plane positioned at an angle of approximately 50 degrees or less with respect to the central axis of the handle portion; and wherein the open attached end extends past the central axis of the handle portion.

9. The suture tool of claim 8, wherein the internal passage of the open ended, hollow, U-shaped tube hook portion has a constant internal diameter extending from the open attached end to the open free end.

10. The suture tool of claim 9, wherein the internal passage of the open ended, hollow, U-shaped tube hook portion has an internal diameter of approximately 0.1 mm to 0.6 mm.

11. The suture tool of claim 10, wherein the spacing between the open free end and the open attached end of the open ended, hollow, U-shaped tube hook portion is approximately 4.0 mm and 7.0 mm.

12. The suture tool of claim 11, wherein the spacing between a base of the open ended, hollow, U-shaped tube hook portion and the open free and open attached ends of the open ended, hollow, U-shaped tube hook portion is approximately 2.0 mm to 3.0 mm.

13. The suture tool of claim 8, wherein the internal passage of the open ended, hollow, U-shaped tube hook portion is tapered from a larger internal diameter at the open attached end to a smaller internal diameter at the open free end.

14. The suture tool of claim 13, wherein the larger internal diameter of the internal passage is approximately 15 mm and the smaller internal diameter of the internal passage is approximately 11 mm.

\* \* \* \* \*